United States Patent
Del Cardayre

(10) Patent No.: US 9,163,267 B2
(45) Date of Patent: Oct. 20, 2015

(54) METATHESIS TRANSFORMATIONS OF MICROBIALLY-PRODUCED FATTY ACIDS AND FATTY ACID DERIVATIVES

(75) Inventor: Stephen B. Del Cardayre, South San Francisco, CA (US)

(73) Assignee: REG Life Sciences, LLC, South San Francisco, CA (US)

( * ) Notice: Subject to any disclaimer, the term of this patent is extended or adjusted under 35 U.S.C. 154(b) by 14 days.

(21) Appl. No.: 13/444,579

(22) Filed: Apr. 11, 2012

(65) Prior Publication Data

US 2013/0274529 A1  Oct. 17, 2013

Related U.S. Application Data

(60) Provisional application No. 61/469,425, filed on Apr. 12, 2011.

(51) Int. Cl.
| | |
|---|---|
| C07C 11/02 | (2006.01) |
| C07C 1/207 | (2006.01) |
| C12P 7/64 | (2006.01) |
| C07C 1/213 | (2006.01) |
| C07C 6/04 | (2006.01) |
| C07C 67/475 | (2006.01) |

(52) U.S. Cl.
CPC .............. *C12P 7/6409* (2013.01); *C07C 1/213* (2013.01); *C07C 6/04* (2013.01); *C07C 67/475* (2013.01); *C12P 7/6436* (2013.01); *C07C 2531/22* (2013.01)

(58) Field of Classification Search
USPC .................................. 585/639, 640; 435/134
See application file for complete search history.

(56) References Cited

U.S. PATENT DOCUMENTS

| | | | | |
|---|---|---|---|---|
| 5,059,532 A | * | 10/1991 | Kimura et al. | 435/134 |
| 7,745,652 B2 | * | 6/2010 | Lysenko et al. | 585/639 |
| 8,071,799 B2 | * | 12/2011 | Olson | 554/163 |
| 8,237,003 B2 | * | 8/2012 | Holtcamp et al. | 556/22 |
| 8,273,694 B2 | * | 9/2012 | Brown et al. | 508/496 |
| 8,299,313 B2 | * | 10/2012 | Takai et al. | 585/637 |
| 8,420,840 B2 | * | 4/2013 | Olson | 554/163 |
| 8,569,560 B2 | * | 10/2013 | Schrodi et al. | 585/639 |
| 8,592,188 B2 | * | 11/2013 | Franklin et al. | 435/134 |
| 2008/0293060 A1 | | 11/2008 | Schirmer et al. | |
| 2009/0264672 A1 | | 10/2009 | Abraham et al. | |
| 2010/0071259 A1 | | 3/2010 | Hu et al. | |
| 2010/0105955 A1 | | 4/2010 | Alibhai et al. | |
| 2010/0105963 A1 | | 4/2010 | Hu et al. | |
| 2010/0145086 A1 | | 6/2010 | Schrodi et al. | |
| 2010/0170826 A1 | | 7/2010 | Friedman et al. | |
| 2010/0199548 A1 | | 8/2010 | del Cardayre et al. | |
| 2010/0216198 A1 | * | 8/2010 | Dubois | 435/134 |
| 2010/0221798 A1 | | 9/2010 | Schirmer et al. | |
| 2010/0235934 A1 | | 9/2010 | Friedman et al. | |
| 2010/0242345 A1 | | 9/2010 | Keasling et al. | |
| 2010/0249470 A1 | | 9/2010 | Schirmer et al. | |
| 2010/0251601 A1 | | 10/2010 | Hu et al. | |
| 2010/0257777 A1 | | 10/2010 | Sanchez-Riera et al. | |
| 2010/0257778 A1 | | 10/2010 | Gaertner et al. | |
| 2010/0274033 A1 | | 10/2010 | Sanchez-Riera et al. | |
| 2011/0072714 A1 | | 3/2011 | Gaertner et al. | |
| 2012/0277452 A1 | * | 11/2012 | Franklin et al. | 554/219 |
| 2012/0289729 A1 | * | 11/2012 | Holtcamp et al. | 556/22 |
| 2013/0130336 A1 | * | 5/2013 | Olson | 435/134 |

FOREIGN PATENT DOCUMENTS

| | | |
|---|---|---|
| WO | 2008119082 | 10/2008 |
| WO | 2008147781 | 12/2008 |
| WO | 2009140696 | 11/2009 |
| WO | 2010062480 | 3/2010 |
| WO | 2010042664 | 4/2010 |
| WO | 2011038132 | 3/2011 |
| WO | 2011038134 | 3/2011 |

OTHER PUBLICATIONS

Bieniek, Michal, et al., "Advanced Fine-Tuning of Grubs/Hoveyda Olefin Metathesis Catalysts: A Further Step toward an Optimum Balance between Antinomic Properties", J. Am. Chem. Soc. (2006) 128, 13652-13653.

Forman, Grant S., et al., "Metathesis of renewable unsaturated fatty acid esters catalysed by a phoban-indenylidene ruthenium catalyst", J. Org. Chem. (2006) 691, 5513-5516.

Galan, Brandon, et al., "A Rapid and Simple Cleanup Procedure for Metathesis Reactions", Org. Lett. (2007) 9, No. 7, 1203-1206.

Grela, Karol, et al., "A Highly Efficient Ruthenium Catalyst for Metathesis Reactions**", Angew, Chem. Int. Ed., (2002) 114, 4038-4040.

Hong, et al., "Prevention of Undesirable Isomerization during Olefin Metathesis", J. Am. Chem. Soc. (2005) 127 17160-17161.

Marvey, Bassie, "Sunflower-based Feedstocks in Nonfood Applications: Perspectives from Olefin Metathesis", Int. J. Mol. Sci., (2008) 9, 1393-1406.

Marvey, et al., "The metathesis of polyunsaturaed fatty esters using the homogeneousW(O-2,6-C6H3X2)2C14/Me4Sn catalytic", J. Mol. Cat. A: Chem., (2004) 213, 151-157.

Nicolaides, C.P. et al., "Metathesis of Fatty Esters Derived from South African Sunflower Oil", J. Am. Oil Chem. Soc. (1990) 67: 1601-1605.

Yang, et al., "Efficient Method for the Synthesis of Chiral Pyrrolidine Derivatives via Ring-Closing Enyne Metathesis Reaction", Org. Lett. (2007) vol. 9, 769-771.

* cited by examiner

*Primary Examiner* — Ellen McAvoy

(74) *Attorney, Agent, or Firm* — Brigitte A. Hajos; REG Life Sciences, LLC

(57) ABSTRACT

Methods of producing olefins, bifunctional molecules, and 7-tetradecene are provided. In some embodiments, the methods comprise subjecting a omega-7-olefinic fatty acid or derivative thereof to metathesis transformation, wherein the omega-7-olefinic fatty acid or derivative thereof was produced in a genetically engineered microorganism.

13 Claims, No Drawings

METATHESIS TRANSFORMATIONS OF MICROBIALLY-PRODUCED FATTY ACIDS AND FATTY ACID DERIVATIVES

CROSS-REFERENCE TO RELATED APPLICATIONS

This application claims priority to and benefit of U.S. Provisional Patent Application No. 61/474,661 filed Apr. 12, 2011, the entire content of which is hereby incorporated by reference.

BACKGROUND

Olefin cross metathesis is an established catalytic process for the breaking and formation of carbon-carbon bonds between olefinic groups of two separate molecules. In a simple system using two different olefin starting materials, six products are formed:

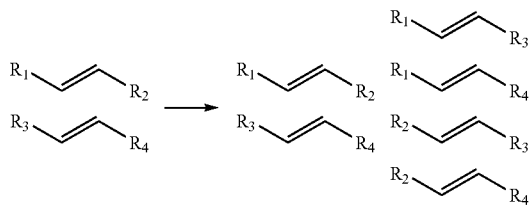

Metathesis chemistry is established and used industrially in the petrochemical industry. Catalysts for these processes include, for example, Grubbs catalysts. Recently, it has been shown that a subset of the Grubbs catalysts can be useful for transforming natural oils, such as those from vegetable or animal sources, to higher value derivatives, such as terminal olefins and bi-functional molecules including diacids, diesters, and omega unsaturated acids and esters. A drawback to this approach, however, is the complexity of the mixture of products that result from the reaction, and the poor yield of the desired product, resulting in challenging recovery and isolation processes, and ultimately more expensive products.

The source of the complexity arises from the natural complexity of natural oils. Natural oils are predominantly composed of a diverse mixture of triacylglycerides (TAGs). TAGs are composed of three fatty acids each esterified to one of the three hydroxyl groups of a glycerol molecule. In each TAG, each of the three fatty acids can vary in structure, having variable chain lengths and level and location of unsaturation. Most common vegetable oils have chain lengths in the C12-C22 range, and each fatty acid moiety may contain three or more olefinic bonds. As each olefinic bond is reactive with the other olefinic bonds in the mixture, metathesis produces a tremendous number of products when natural oils are used as a starting material. Indeed, there is an exponential increase in the number of products with each additional olefin in the mixture.

Thus, a less complex and more specific set of olefinic reactants would result in a less diverse more specific set of products, and would be a much more cost effective way to make a particular desired olefin.

SUMMARY

In some embodiments, a method of producing an olefin is provided. In some embodiments, the method comprises contacting a composition comprising at least one omega-7-olefinic fatty acid or derivative thereof with a cross metathesis catalyst under conditions allowing a metathesis transformation, wherein the at least one omega-7-olefinic fatty acid or derivative thereof was produced in a genetically engineered microorganism. In some embodiments, the omega-7-olefinic fatty acid or derivative thereof has the structure:

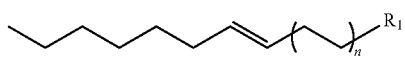

wherein n is an integer from 1 to 7, and $R_1$ is selected from methyl ester, ethyl ester, wax ester, amine, amide, carboxylic acid, alcohol, alkane and aldehyde.

In some embodiments, a method of producing a bifunctional molecule is provided, wherein the bifunctional molecule comprises a first terminal functional group and a second terminal functional group. In some such embodiments, the method comprises contacting a composition comprising a first olefin and a second olefin with a cross metathesis catalyst under conditions allowing a metathesis transformation, wherein the first olefin comprises a first terminal functional group, and the second olefin comprises a second terminal functional group, and wherein at least one of the first olefin and the second olefin is a omega-7-olefinic fatty acid or derivative thereof that was produced in a genetically engineered microorganism. In some embodiments, the first terminal functional group and the second terminal functional group are independently selected from methyl ester, ethyl ester, wax ester, amine, amide, carboxylic acid, alcohol, alkane and aldehyde. In some embodiments, the first terminal functional group and the second terminal functional group are different. In some embodiments, the first terminal functional group and the second terminal functional group are the same. In some embodiments, the first olefin and the second olefin are the same. In some embodiments, the first olefin and the second olefin are each independently a omega-7-olefinic fatty acid or derivative thereof with the structure:

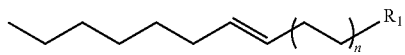

wherein n is an integer from 1 to 7, and $R_1$ is selected from methyl ester, ethyl ester, wax ester, amine, amide, carboxylic acid, alcohol, alkane and aldehyde.

In some embodiments, a method of producing a bifunctional molecule is provided, wherein the bifunctional molecule comprises a terminal functional group and a terminal olefin. In some embodiments, the method comprises contacting a composition comprising a omega-7-olefinic fatty acid or derivative thereof and ethylene with a cross metathesis catalyst under conditions allowing a metathesis transformation, wherein the omega-7-olefinic fatty acid or derivative thereof comprises a terminal functional group, and wherein the omega-7-olefinic fatty acid or derivative thereof was produced in a genetically engineered microorganism. In some embodiments, the terminal functional group is selected from methyl ester, ethyl ester, wax ester, amine, amide, carboxylic acid, alcohol, alkane and aldehyde.

In some embodiments, a method of producing 7-tetradecene is provided. In some embodiments, the method comprises contacting a composition comprising a omega-7-olefinic fatty acid or derivative thereof with a metathesis catalyst under conditions allowing a metathesis transformation, wherein the omega-7-olefinic fatty acid or derivative thereof was produced in a genetically engineered microorganism.

In some embodiments, a method of producing 1-octene is provided. In some embodiments, the method comprises contacting a composition comprising a omega-7-olefinic fatty acid or derivative thereof with a cross metathesis catalyst and ethylene under conditions allowing a metathesis transformation, wherein the omega-7-olefinic fatty acid or derivative thereof was produced in a genetically engineered microorganism.

In some embodiments, a method of producing an olefin comprises (a) culturing a genetically engineered host cell in the presence of a carbon source under conditions allowing production of a omega-7-olefinic fatty acid or derivative thereof; (b) isolating the omega-7-olefinic fatty acid compound; and (c) forming a composition comprising the omega-7-olefinic fatty acid or derivative thereof and a cross metathesis catalyst and incubating the composition under conditions allowing a metathesis transformation.

In some embodiments, a genetically engineered microorganism is genetically engineered to express or overexpress a gene encoding an ester synthase, in some embodiments, a genetically engineered microorganism is genetically engineered to express or overexpress a gene encoding a thioesterase, a gene encoding an acyl-CoA synthase, and a gene encoding an ester synthase.

DETAILED DESCRIPTION

In order to cost-effectively produce particular desired olefins using metathesis transformations, starting materials that are less complex than natural oils are needed. To address this problem, the present invention provides for the production of particular desired fatty acids, which, when used in metathesis transformations, result in a higher yield of specific olefinic products than is possible using natural oils as a starting material. The result is an ability to more efficiently design the product output, increase its yields, decrease the complexity of the product mixture, simplify recovery, and improve the overall economics of recovery. In addition, the present invention provides novel routes to highly desirable molecules.

The articles "a" and "an" are used herein to refer to one or to more than one (i.e., to at least one of the grammatical object of the article. By way of example, "an element" means one element or more than one element. The terms "comprising," "having," "including," and "containing" are to be construed as open-ended terms (e.g., meaning "including, but not limited to,") unless otherwise noted.

Exemplary Fatty Acid Production Using Genetically Engineered Microorganisms

The fatty acid compounds produced by the genetically engineered microorganisms are not triacylglycerides (TAGS), and they contain no TAG, glyceride, or glycerol. Further, in contrast to most organisms from which natural oils are derived, microbial fatty acids, such as those from *E. coli*, are not poly-olefinic. Indeed, microbial fatty acids are generally either saturated or mono-olefinic, with the olefinic bond typically located at the omega-7 position. In addition, by producing fatty acids using genetically engineered microorganisms, the chain length of the fatty acids and fatty acid derivatives produced can be controlled, further decreasing the complexity of the subsequent metathesis reaction reagents and products. As a further advantage of the present methods, producing fatty acids in genetically engineered microorganisms allows for the incorporation of diverse chemistries in place of the fatty acid moiety found in most natural oils. For example, fatty esters, alcohols, amines, etc. can be produced by the genetically engineered microorganisms, and used as reactants for olefin cross metathesis transformations, allowing for a much broader range greater control of substituents in the metathesis transformation products than possible with natural oils.

Nonlimiting exemplary methods for producing particular fatty acids and derivative products by genetically engineering microbial fatty acid metabolism are described, e.g., in U.S. Publication Nos. US2010/0242345, US2010/0071259, US2010/0257777, US2010/0105955, US2010/0221798, US2010/0249470, US2010/0170826, US2010/0199548, US2010/0274033, US20080293060, US20100105963, US20100235934, US20100257778, US20100251601, US20110072714; and PCT Publication Nos. WO2008/119082, WO 2008/147781, WO2009/140696, WO 2010/062480, WO2010/042664, WO2011/038134 and WO2011/038132, each of which is incorporated by reference herein in its entirety for any purpose.

In some embodiments, a omega-7-olefinic fatty acid or derivative thereof having the structure:

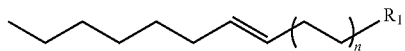

wherein n is an integer from 1 to 7, and $R_1$ is selected from methyl ester, ethyl ester, wax ester, amine, amide, carboxylic acid, alcohol, alkane and aldehyde, is produced in a genetically engineered microorganism. In some embodiments, n is an integer from 1 to 5. In some embodiments, when R1 is carboxylic acid, the compound is referred to as a fatty acid.

In various embodiments, a omega-7-olefinic fatty acid or derivative thereof is produced by culturing a host cell in the presence of a carbon source, wherein the host cell has been genetically engineered such that it produces the omega-7-olefinic fatty acid or derivative thereof. As used herein, the phrase "carbon source" refers to a substrate or compound suitable to be used as a source of carbon for prokaryotic or simple eukaryotic cell growth. Carbon sources can be in various forms, including, but not limited to polymers, carbohydrates, acids, alcohols, aldehydes, ketones, amino adds, peptides, and gases (e.g., CO and $CO_2$). These include, for example, various monosaccharides, such as glucose, fructose, mannose, and galactose; oligosaccharides, such as fructo-oligosaccharide and galacto-oligosaccharide; polysaccharides such as xylose and arabinose; disaccharides, such as sucrose, maltose, and turanose; cellulosic material, such as methyl cellulose and sodium carboxymethyl cellulose; saturated or unsaturated fatty acid esters, such as succinate, lactate, and acetate; alcohols, such as methanol, ethanol, propanol, or mixtures thereof. The carbon source can also be a product of photosynthesis, including, but not limited to, glucose. In some embodiments, a carbon source is biomass (i.e., a carbon source derived from biological: material, such as plant matter). In some embodiments, a carbon source is glucose.

In some embodiments, the genetically engineered microorganism has been genetically engineered to increase and/or decrease the expression of one or more endogenous fatty acid metabolism genes, which encode one or more fatty acid metabolism enzymes. In some embodiments, the genetically engineered microorganism has been genetically engineered such that it expresses an exogenous fatty acid metabolism gene, which encodes a fatty acid metabolism enzyme. Nonlimiting exemplary fatty acid metabolism enzymes include fatty acid synthases, thioesterases, acyl-CoA synthases, ester synthases, wax synthases, diacylglycerol acyltransferases, alcohol dehydrogenases, alcohol acyltransferases, acyl-CoA reductases, and fatty-alcohol forming acyl-CoA reductases.

In some embodiments, a microorganism has been genetically engineered to overexpress a gene encoding a thioesterase, a gene encoding an acyl-CoA synthase, and a gene encoding an ester synthase. See, e.g., PCT Publication No. WO2011/038134, In some such embodiments, the genetically engineered microorganism produces a omega-7-olefinic fatty ester. In some embodiments, the genetically engineered microorganism produces a omega-7-olefinic fatty acid methyl ester and/or a omega-7-olefinic fatty acid ethyl ester.

In some embodiments, a microorganism has been genetically engineered to overexpress a gene encoding an ester synthase. See, e.g., PCT Publication No. WO2011/038132. In some such embodiments, the genetically engineered microorganism produces a omega-7-olefinic fatty ester. In some embodiments, the genetically engineered microorganism produces a omega-7-olefinic fatty acid methyl ester and/or a omega-7-olefinic fatty acid ethyl ester.

In some embodiments, a microorganism has been genetically engineered to express a gene encoding a fatty alcohol biosynthetic peptide. See, e.g., PCT Publication No. WO2010/062480. In some embodiments, the microorganism has been genetically engineered to express a gene encoding, carboxylic acid reductase. In some such embodiments, the genetically engineered microorganism produces a omega-7-olefinic fatty alcohol.

In some embodiments, a microorganism has been genetically engineered to express a gene encoding a fatty aldehyde biosynthetic peptide. See, e.g., PCT Publication Nos. WO2010/042664 and WO2009/140696. In some embodiments, the microorganism has been genetically engineered to express a gene encoding carboxylic acid reductase. In some such embodiments, the genetically engineered microorganism produces a omega-7-olefinic fatty aldehyde.

In some embodiments, a genetically engineered microorganism produces a fatty acid wax ester. See, e.g., PCT Publication No. WO2008/119082.

Nonlimiting exemplary microorganisms that can be genetically engineered to produce omega-7-olefinic fatty acids or derivatives thereof include microorganisms from a genus selected from *Escherichia, Bacillus, Lactobacillus, Rhodococcus, Pseudomonas, Aspergillus, Trichoderma, Neurospora, Fusarium, Humicola, Rhizomucor, Kluyveromyces, Pichia, Mucor, Myceliophtora, Penicillium, Phanerochaete, Pleurotus, Trametes, Chrysosporium, Saccharomyces, Stenotrophamonas, Schizosaccharomyces, Yarrowia,* and *Streptomyces.* In some embodiments, a genetically engineered microorganism is selected from *Bacillus lentus, Bacillus brevis, Bacillus stearothermophilus, Bacillus licheniformis, Bacillus alkaiophiius, Bacillus coagulans, Bacillus circulans, Bacillus pumilis, Bacillus thuringiensis, Bacillus clausii, Bacillus megaterium, Bacillus subtilis, Bacillus amyloliquefaciens, Trichoderma koningii, Trichoderma viride, Trichoderma reesei, Trichoderma longibrachiatum,* an *Aspergillus awarnori,* an *Aspergillus furnigates,* an *Aspergillus foetidus,* an *Aspergillus nidulans,* an *Aspergillus niger,* an *Aspergillus oryzae, Humicola insolens, Humicola lanuginose, Rhodococcus opacus, Rhizomucor miehei, Mucor michei, Streptomyces lividans* or *Streptomyces murinus,* an *Actinomycetes, Saccharomyces cerevisiae,* CHO, COS, VERO, BHK, HeLa, Cvl, an MDCK, 293, 3T3, and PC 12.

As used herein, "conditions glowing production" refers to any fermentation conditions that allow a production host cell to produce a desired product, such as a omega-7-olefinic Fatty acid or derivative thereof. Fermentation conditions usually comprise many parameters. Exemplary conditions include, but are not limited to, temperature ranges, levels of aeration, and media composition. Each of these conditions, individually and/or in combination, allows the production host to grow. Exemplary media include broths and/or gels. Generally, a suitable medium includes a carbon source (e.g., glucose, fructose, cellulose, etc.) that can be metabolized by the microorganism directly. In addition, enzymes can be used in the medium to facilitate the mobilization (e.g., the depolymerization of starch or cellulose to fermentable sugars) and subsequent metabolism of the carbon source.

Exemplary Metathesis Transformation

Olefin metathesis transformation results in the exchange of substituents between separate olefin molecules, i.e. a transalkylidenation.

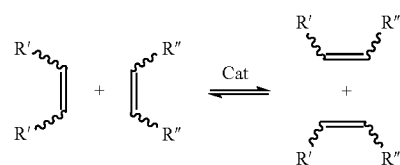

This reaction was first used in petroleum reformation for the synthesis of higher olefins (Shell higher olefin process—SHOP), with nickel catalysts under high pressure and high temperatures. Today, even polyenes with MW>250,000 are produced industrially in this way.

Nonlimiting exemplary metathesis transformations for laboratory use include ring closure between terminal vinyl groups; cross metathesis, or intermolecular reaction of vinyl groups; and ring-opening of strained alkenes. When starting materials with terminal vinyl groups are used, the equilibrium can be driven by the removal of the product ethylene from the reaction mixture. To drive the equilibrium in ring opening metathesis, in some instances, excess of a second alkene is used. Alternatively, the equilibrium in a ring opening metathesis can be driven simply by a loss of ring strain in the product.

New catalysts have made possible the development of metathesis transformations for a wide array of starting materials. For example, catalysts have been developed that are more stable, easier to handle, and tolerate a wider range functional groups on the reactants. Nonlimiting exemplary catalysts include Grubbs catalysts, 1 and 2, and Schrock catalyst, 3.

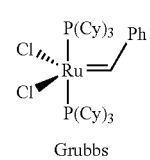

Grubbs

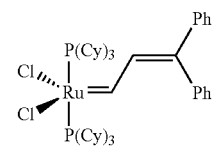

-continued

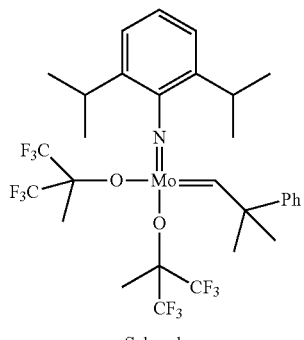

Schrock

The Schrock catalysts are, in certain embodiments, more active and are useful in the conversion of sterically demanding substrates. In some embodiments, Grubbs catalysts tolerate a wide variety of functional groups.

The second generation Grubbs catalysts are, in some embodiments, more stable than prior Grubbs catalysts, and also more active. See, e.g., Grela et al., *Angew. Chem. Int. Ed.*, 2002, 114, 4038.

Activity:
2 < 1b < 4 < 5 ⟹

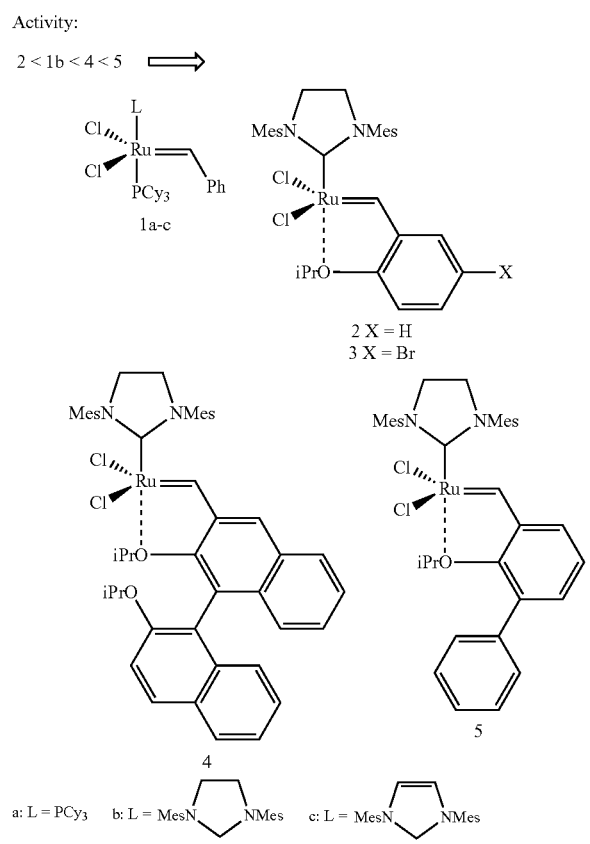

a: L = PCy$_3$   b: L = MesN⟨⟩NMes   c: L = MesN⟨⟩NMes

Use of catalyst 1b is described, for example, in Hong et al., *J. Am. Chem. Soc.*, 2005, 127: 17160-17161; and Galan et al., *Org. Lett.*, 2007, 9: 1203-1206. Use of catalyst 1a is described, for example, in Yang, et al., *Org. Lett.*, 2007, 9: 769-771. Use of catalyst 6, below, is described, for example, in Bieniek et al., *J. Am. Chem. Soc.*, 2006, 128: 13652-13653.

catalyst:

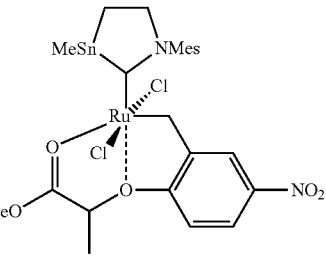

Further nonlimiting exemplary catalysts for metathesis transformations include the phoban-indenylidene complex (Forman et al., *J. Organomet. Chem.*, 2006, 691: 5513-5516).

Various metathesis transformations on natural oils have been described. For example, U.S. Published Application No. US2010/0145086, which is incorporated herein by reference in its entirety for any purpose, describes various cross metathesis catalysts, and metathesis transformations of, for example, soybean oil, soy fatty acid methyl esters, and canola fatty acid methyl esters. Similarly, U.S. Published Application No. US2009/0264672, which is incorporated herein by reference in its entirety for any purpose, also describes various metathesis catalysts, and metathesis transformation of soybean oil. Further exemplary metathesis of fatty acid esters in various seed oils are described, e.g., in Marvey et al. *J. Mol. Catal. A: Chem.*, 2003, 201: 297-308; Nicolaides et al., *J. Am. Oil Chem. Soc.*, 1990, 67: 1601-1605; and Marvey, *Int. J. Mol. Sci.*, 2008, 9: 1393-1406. The use of natural oils in metathesis transformations leads to a complex mixture of products, making isolation of any one particular desired molecule expensive and difficult.

Exemplary Methods

Methods of producing olefinic compounds are provided herein. Such methods comprise contacting a composition comprising at least one olefin with a cross metathesis catalyst under conditions allowing a metathesis transformation, wherein at least one olefin was produced in a genetically engineered microorganism. In some embodiments, such methods comprise contacting a composition comprising at least one omega-7-olefinic fatty acid or derivative thereof with a cross metathesis catalyst under conditions allowing a metathesis transformation, wherein at least one omega-7-olefinic fatty acid or derivative thereof was produced in a genetically engineered microorganism. In some embodiments, each omega-7-olefinic fatty acid or derivative thereof has the structure:

wherein n is an integer from 1 to 7, and $R_1$ is selected from methyl ester, ethyl ester, wax ester, amine, amide, carboxylic acid, alcohol, alkane and aldehyde. In some embodiments, the composition comprises one omega-7-olefinic fatty acid or derivative thereof. In some embodiments, the composition comprises two different omega-7-olefinic fatty acids or derivatives thereof. In some embodiments, the composition comprises more than two different omega-7-olefinic fatty acids or derivatives thereof.

In some embodiments, methods of producing bifunctional molecules are provided. In some such embodiments, the bifunctional molecule comprises a first terminal functional group and a second terminal functional group. In some embodiments, the method comprises contacting a composition comprising a first olefin with a first terminal functional group, and a second olefin with a second terminal functional group, with a cross metathesis catalyst under conditions allowing a metathesis transformation. In some embodiments, at least one of the first olefin and the second olefin is a omega-7-olefinic fatty acid or derivative thereof that was produced in a genetically engineered microorganism. Using such a method, in some embodiments, a bifunctional molecule can be produced, which is a straight-chain alkene with a single double bond and terminal functional groups on each end. Thus, in some embodiments, the method produces a bifunctional molecule having the structure:

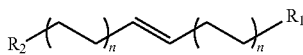

wherein n is an integer from 1 to 7, m is an integer from 1 to 7, and $R_1$ and $R_2$ are independently selected from methyl ester, ethyl ester, wax ester, amine, amide, carboxylic acid, alcohol, alkane and aldehyde. $R_1$ and $R_2$ may be the same or different. Similarly, n and m may be the same or different. In some embodiments, when $R_1$ and $R_2$ are the same, and n and m are the same, the metathesis transformation reaction comprises one olefin.

In some embodiments, a bifunctional molecule comprises a terminal functional group and a terminal olefin. In some such embodiments, the method comprises contacting a composition comprising a omega-7-olefinic fatty acid or derivative thereof with a cross metathesis catalyst and ethylene under conditions allowing a metathesis transformation, wherein the omega-7-olefinic fatty acid or derivative thereof comprises a terminal functional group, and wherein the omega-7-olefinic fatty acid or derivative thereof was produced in a genetically engineered microorganism. In some such embodiments, the bifunctional molecule has the structure:

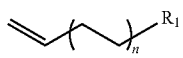

wherein n is an integer from 1 to 7, and $R_1$ is selected from methyl ester, ethyl ester, wax ester, amine, amide, carboxylic acid, alcohol, alkane and aldehyde.

In some embodiments, methods of producing 7-tetradecene are provided. In some such embodiments, the method comprises contacting a composition comprising a omega-7-olefinic fatty acid or derivative thereof with a cross metathesis catalyst under conditions allowing a metathesis transformation, wherein the omega-7-olefinic fatty acid or derivative thereof was produced in a genetically engineered microorganism. When 7-tetradecene is produced, the functionalized portion of the fatty acid or derivative thereof is not part of the desired product. Thus, the fatty acid or derivative thereof that is the purest, gives the highest yield of 7-tetradecene, the fastest reaction, or has another desirable property, can be selected for use in the method, independent of the functional group on the fatty acid or derivative thereof.

In some embodiments, methods of producing 1-octene are provided. In some such embodiments, the method comprises contacting a composition comprising a omega-7-olefinic fatty acid or derivative thereof with a cross metathesis catalyst and ethylene under conditions allowing a metathesis transformation, wherein the omega-7-olefinic fatty acid or derivative thereof was produced in a genetically engineered microorganism. When 1-octene is produced, the functionalized portion of the fatty acid or derivative thereof is not part of the desired product. Thus, the fatty acid or derivative thereof that is the purest, gives the highest yield of 1-octene, the fastest reaction, or has another desirable property, can be selected for use in the method, independent of the functional group on the fatty acid or derivative thereof.

In some embodiments, a method of producing an olefin comprises (a) culturing a genetically engineered host cell in the presence of a carbon source under conditions allowing production of a omega-7-olefinic fatty acid or derivative thereof; (b) isolating the omega-7-olefinic fatty acid compound; and (c) forming a composition comprising the omega-7-olefinic fatty acid or derivative thereof and a cross metathesis catalyst and incubating the composition under conditions allowing a metathesis transformation.

In some embodiments, the genetically engineered microorganism used to produce the omega-7-olefinic fatty acid or derivative thereof used as a reagent in the metathesis transformation is genetically engineered to express or overexpress a gene encoding an ester synthase. In some embodiments, the genetically engineered microorganism used to produce the omega-7-olefinic fatty acid or derivative thereof used as a reagent in the metathesis transformation
is genetically engineered to express or overexpress a gene encoding a thioesterase, a gene encoding an acyl-CoA synthase, and a gene encoding an ester synthase. Nonlimiting exemplary genetically engineered microorganisms are discussed herein, and in the documents cited herein, each of which is incorporated by reference in its entirety for any purpose.

The following examples are intended to be purely exemplary of the invention and should not be considered to limit the invention in any way.

EXAMPLES

Example 1

Production of 7-tetradecene

Straight-chain monoolefins, such as 7-tetradecene, are used in the production of various surfactants, lubricants, etc. The fatty acids produced by the genetically engineered microorganisms discussed herein are omega-7-olefinic. Upon cross metathesis, a omega-7-olefinic fatty acid or fatty acid derivative produces 7-tetradecene. See reaction scheme (I). The 7-tetradecene results from the combination of the C7 alkyl moieties of the reactants, and, in some embodiments, constitutes approximately 20% to 35% of the reaction product.

Scheme (I)

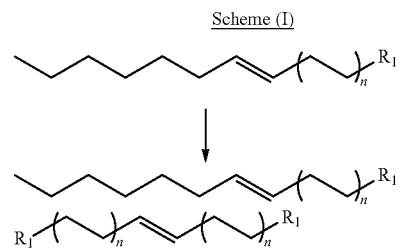

-continued

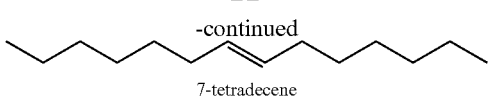
7-tetradecene 7-tetradecene is therefore a major and consistent product of a metathesis transformation using genetically engineered microorganism-derived fatty acids, regardless of the chemical functionality (i.e., "R groups") on the fatty acids. Thus, using the present methods, 7-tetradecene can be produced in high yields from fatty acids without the use of an added reactant, such as ethylene, which is used to drive alternative reactions.

Example 2

Production of Diesters

As discussed herein, microorganisms can be genetically engineered to produce fatty acids with a variety of functional groups, such as esters, amines, etc. Thus, bifunctional molecules can be made by using a particular functionalized fatty acid from a genetically engineered microorganism in a metathesis transformation.

As shown in reaction scheme (II), diester molecules can be made by using a fatty acid methyl ester produced in high yield by a genetically engineered microorganism in a methathesis transformation.

Scheme (II)

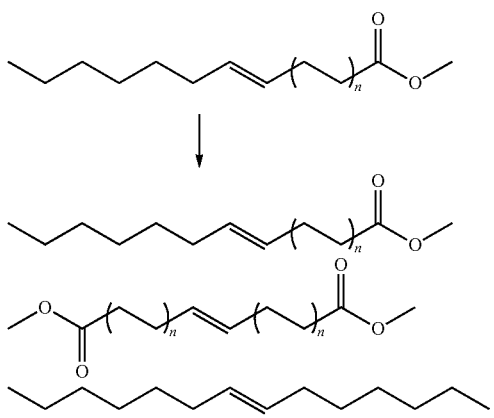

In some embodiments, the diester product constitutes approximately 20% to 35% of the resulting product mixture. Further, the diester can be subsequently hydrolyzed to a diacid using methods in the art, and the resulting diacids can be used in polyamide production, or in the synthesis of various other compounds, such as flavoring agents and fragrances.

If the starting fatty acid is an alcohol rather than a methyl ester, a mixture comprising diols, in addition to 7-tetradecene, would result. Similarly, if the starting fatty acid is a mixture of fatty acid methyl esters and alcohols, the mixture resulting from metathesis transformation would comprise diesters, diols, and omega-hydroxy esters, in addition to 7-tetradecene.

Thus, based on the present disclosure, one skilled in the art can produce a particular product of mixture of products by subjecting a desired fatty acid or mixture of fatty acids produced by the genetically engineered microorganisms discussed herein to a metathesis transformation.

Example 3

Production of 1-octene and Terminal Olefins

Reaction of various omega-7-olefinic compounds produced by genetically engineered microorganisms with ethylene in a metathesis transformation produces 1-octene. In some embodiments, the reaction is driven to stoichiometric completion, for example, under high ethylene concentrations and pressures, or through the selective removal of the product under vacuum. See reaction scheme (III).

Scheme (III)

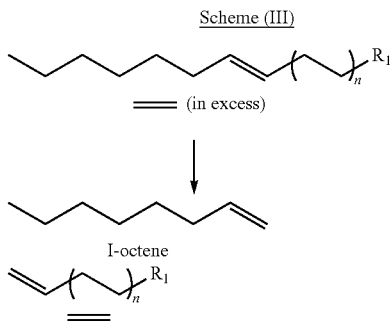

In addition to the 1-octene produced by this method, an equal amount of a terminal olefin with the functional group of the original fatty acid is also produced. Such terminal olefins are also useful. For example, bifunctional molecules comprising a terminal olefin and a terminal functional group, such as an amine or ester, can be used as cross-linking reagents.

Each of the foregoing reactions relies on the purity of the starting fatty acid in order to produce the desired molecule(s) in commercially and economically viable quantities. The use of genetically engineered microorganisms provides an economically feasible way of producing fatty acid compositions with high proportions of a single fatty acid.

The invention claimed is:

1. A method of producing an olefin comprising contacting a composition comprising at least one omega-7-olefinic fatty acid or derivative thereof with a cross metathesis catalyst under conditions allowing a cross metathesis transformation, wherein the at least one omega-7-olefinic fatty acid or derivative thereof was produced in a genetically engineered microorganism.

2. The method of claim 1, wherein the omega-7-olefinic fatty acid or derivative thereof has the structure:

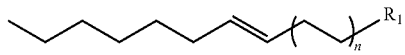

wherein n is an integer from 1 to 7, and R1 is selected from methyl ester, ethyl ester, wax ester, amine, amide, carboxylic acid, alcohol, alkane, and aldehyde.

3. The method of claim 1 for producing 7-tetradecene.

4. The method of claim 1, for producing 1-octene comprising contacting a composition comprising a omega-7-olefinic fatty acid or derivative thereof with a cross metathesis catalyst and ethylene under conditions allowing a metathesis transformation, wherein the fatty acid derivatives have a fraction of modern carbon of about 1.003 to about 1.5.

5. An olefin produced by cross-metathesis according to the method of claim 1, wherein said olefin has a fraction of modern carbon of about 1.003 to about 1.5.

6. A method of producing a bifunctional molecule, wherein the bifunctional molecule comprises a first terminal functional group and a second terminal functional group, comprising contacting a composition comprising a first olefin and an additional compound with a metathesis catalyst under conditions allowing a cross metathesis transformation, wherein the first olefin comprises a first terminal functional group, wherein the first olefin is a omega-7-olefinic fatty acid or derivative thereof that was produced in a genetically engineered microorganism.

7. The method of claim 6, wherein the first terminal functional group and the second terminal functional group are independently selected from methyl ester, ethyl ester, wax ester, amine, amide, carboxylic acid, alcohol, alkane, and aldehyde.

8. The method of claim 7, wherein the first terminal functional group and the second terminal functional group are different.

9. The method of claim 7, wherein the first terminal functional group and the second terminal functional group are the same.

10. The method of claim 9, wherein the additional compound is a second olefin.

11. The method of claim 10, wherein the first olefin and the second olefin are each independently an omega-7-olefinic fatty acid or derivative thereof with the structure:

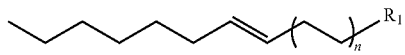

wherein n is an integer from 1 to 7, and RI is selected from methyl ester, ethyl ester, wax ester, amine, amide, carboxylic acid, alcohol, alkane- and aldehyde.

12. The method of claim 6, wherein the bifunctional molecule comprises a terminal olefin as the second terminal functional group, wherein said first olefin is a omega-7-olefinic fatty acid or derivative thereof and said additional compound is ethylene.

13. The method of claim 12, wherein the terminal functional group is selected from methyl ester, ethyl ester, wax ester, amine, amide, carboxylic acid, alcohol, alkane and aldehyde.

* * * * *